United States Patent
Roessl et al.

(10) Patent No.: US 7,822,169 B2
(45) Date of Patent: Oct. 26, 2010

(54) NOISE REDUCTION IN DUAL-ENERGY X-RAY IMAGING

(75) Inventors: Ewald Roessl, Ellerau (DE); Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 162 days.

(21) Appl. No.: 12/293,845

(22) PCT Filed: Mar. 14, 2007

(86) PCT No.: PCT/IB2007/050877

§ 371 (c)(1),
(2), (4) Date: Sep. 22, 2008

(87) PCT Pub. No.: WO2007/110794

PCT Pub. Date: Oct. 4, 2007

(65) Prior Publication Data

US 2009/0135998 A1    May 28, 2009

(30) Foreign Application Priority Data

Mar. 29, 2006  (EP) .................................. 06111881

(51) Int. Cl.
*A61B 6/00* (2006.01)
(52) U.S. Cl. ................... 378/5; 378/4; 378/98
(58) Field of Classification Search ........... 378/5, 378/98, 98.11, 98.12
See application file for complete search history.

(56) References Cited

U.S. PATENT DOCUMENTS

| | | | | |
|---|---|---|---|---|
| 4,029,963 A | * | 6/1977 | Alvarez et al. ............ | 378/5 |
| 4,463,375 A | * | 7/1984 | Macovski ................ | 378/98.12 |
| 5,115,394 A | | 5/1992 | Walters | |
| 5,221,843 A | | 6/1993 | Alvarez | |
| 5,436,829 A | * | 7/1995 | Hartley .................... | 378/6 |
| 5,568,530 A | | 10/1996 | Saito et al. | |
| 5,965,897 A | | 10/1999 | Elkind et al. | |
| 6,408,050 B1 | | 6/2002 | Han et al. | |
| 6,614,874 B2 | * | 9/2003 | Avinash .................. | 378/62 |
| 7,706,497 B2 | * | 4/2010 | Hsieh et al. .............. | 378/5 |
| 2002/0094062 A1 | * | 7/2002 | Dolazza et al. ........... | 378/98.9 |
| 2006/0274877 A1 | * | 12/2006 | Noshi et al. ............. | 378/4 |

FOREIGN PATENT DOCUMENTS

| WO | 2005009206 A2 | 2/2005 |
|---|---|---|
| WO | 2005092187 A1 | 10/2005 |

* cited by examiner

*Primary Examiner*—Edward J Glick
*Assistant Examiner*—Alexander H Taningco (57) ABSTRACT

It is described a method for reducing noise of X-ray attenuation data related to a first and second spectral X-ray data acquisition. The method comprises the steps of (a) acquiring data representing the X-ray attenuation behavior of a region of interest, (b) determining a first and a second attenuation-base line integral for the first and the second X-ray acquisition, respectively, and (c) calculating expected first and second signal to noise ratios for the first and the second attenuation-base line integral based on given signal to noise ratios for the first and second spectral X-ray data acquisition, respectively. The method further comprises the steps of (d) repeating the above mentioned steps of determining the attenuation-base line integrals and calculating the expected signal to noise ratios for a further first spectral X-ray data acquisition and (e) selecting improved spectral X-ray data acquisitions in order to enhance the overall signal to noise ratio of a final X-ray image.

18 Claims, 3 Drawing Sheets

NOISE REDUCTION IN DUAL-ENERGY X-RAY IMAGING

The present invention relates to the field of dual energy X-ray imaging. Thereby, two different images of one and the same region of interest are obtained, whereby two spectral different X-ray data acquisitions are used. In particular, the present invention relates to a method for reducing the statistical noise of X-ray attenuation data corresponding to two spectrally different X-ray data acquisitions.

The present invention further relates to a data processing device for reducing statistical noise of X-ray attenuation data related to two spectral different X-ray data acquisitions.

Further, the present invention relates to radiography system for dual energy X-ray imaging.

Furthermore, the present invention relates to a computer-readable medium and to a program element having instructions for executing the above-mentioned method for reducing the statistical noise of X-ray attenuation data related to two spectral different X-ray data acquisitions.

Today, doctors and technicians commonly have access to very sophisticated medical diagnostic X-ray imaging devices. Typically during the operation of an X-ray imaging device, an X-ray source emits X-ray photons under very controlled circumstances. The X-ray photons travel through a region of interest (ROI) of a patient under examination and impinge upon a detector. In the past, X-ray imaging devices employed rudimentary film based detectors. However, recent developments have led to solid-state detectors comprised of a grid of discrete detector elements that individually respond to exposure by X-ray photons. Regardless of the detector used, however, the goal remains the same, namely, to produce a clear resultant image of preselected ROI (e.g. specific types of tissues) within an object of interest.

There is an inherent difficulty associated with producing a clear resultant image, however. In particular, because the X-ray photons travel through the entire patient, the image formed on the detector is a superposition of all the anatomic structures through which X-ray photons pass, including the preselected ROI. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

Attempts to reduce the effects of anatomic noise included, for example, "dual-energy" imaging. When employing dual-energy imaging, a doctor or technician acquired two images each with different average X-ray photon energies. Because different internal structures absorb different X-ray photon energies to different extents, it was possible to combine the two resultant images to suppress anatomic noise. Dual-energy techniques typically proceed in one of two ways.

A first approach uses two stacked detectors. A single exposure then produces a first image in a front detector. Some X-ray photons continue through the front detector to impinge upon a rear detector. The front and rear detectors are designed to sense different average energies, thereby producing two images of the ROI corresponding to two distinct average X-ray photon energies. A second approach uses a single detector and two exposures each with different average X-ray photon energy.

U.S. Pat. No. 6,408,050 B1 discloses a method for energy dependent imaging of a region of interest. The method includes the step of exposing an X-ray detector to X-ray photons during an examination period, and separating the X-ray photons into two groups, those with energies above a selected energy threshold, and those with energies below a selected energy threshold. The X-ray photons with energy above the threshold are counted to provide a first energy photon count, while the X-ray photons with energy below the threshold are counted to provide a second energy photon count. The method stores the first energy photon count and the second energy photon count in a memory as examination data, and produces an image by applying an image processing technique to the examination data.

WO 2005/092187 A1 discloses an apparatus and a method for an angiographic imaging. Thereby, an X-ray tube is energized and a myocardium is imaged while contrast agent is infused to the coronary arteries of the subject. Single photon counting data acquired with the detector while two thresholds are set to form simultaneously low-energy images and high-energy images. The images are processed and displayed. The thresholds levels are adjusted by using radioactive sources, which emit, among other radiation, X-ray photons with a defined energy of e.g. 32 keV. A threshold level of a low level discriminator is gradually increased for each readout channel while the output counting rate is monitored. As the discriminator level increases over 32 keV, the count rate drops. The threshold level is set at a level slightly below the drop level.

In X-ray imaging of human patients it is always a challenge to reduce the radiation dose to a minimum. In order to achieve this challenge modern X-ray detectors having a high efficiency in photon counting are very helpful. Such X-ray detectors typically comprise a plurality of detector elements arranged within an array in order to provide for a two dimensional spatial resolution. However, when the radiation dose is reduced, the photon count rate for each detector element is also reduced. This has the consequence, that the acquired images exhibit a noisy background. In other words, the signal to noise ratio (SNR) is reduced.

There may be a need for a noise reduction in dual-energy X-ray imaging in order to improve the SNR of the acquired images.

This need may be met by the subject matter according to the independent claims. Advantageous embodiments of the present invention are described by the dependent claims.

According to a first aspect of the present invention there is provided a method for reducing statistical noise of X-ray attenuation data related to two spectral different X-ray data acquisition, a first spectral X-ray data acquisition and a second spectral X-ray data acquisition, in particular for enhancing the overall signal to noise ratio for dual energy X-ray imaging.

The described method comprises the steps of (a) acquiring data representing the X-ray attenuation behavior of a region of interest within an object of interest, (b) determining a first attenuation-base line integral for the first spectral X-ray data acquisition and a second attenuation-base line integral for the second spectral X-ray data acquisition, respectively, for a predetermined X-ray beam path traversing the region of interest, and (c) calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively.

The described method further comprises the steps of (d) repeating the above-mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition and (e) selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral.

This aspect of the invention is based on the idea that because of photon statistic reasons the signal to noise ratio (SNR) of an image strongly depends on the photon count rates for each pixel of the image. This hold also for dual-energy imaging, wherein two images obtained with different average X-ray energies may be combined for a final image. This combination can be carried out by means of an appropriate image processing procedure. This combination can also be done virtually by a physician who takes the information provided by the two images in order to provide a diagnosis based on his experience with separate images obtained by means of dual-energy imaging.

According to the described method the two spectral characteristics of two different X-ray measurements are selected such that each of the two images benefits more or less equally from a sufficient count rate. In other words, by taking into account the individual SNR of the two images a maximum overall SNR of the final image may be achieved. This means that the spectral measurements are performed in such a way that the count rates for both images have at least an acceptable level in order not to have one image with a very high SNR and another image with a very low SNR.

The object of interest is e.g. a human body or an animal body. The region of interest is typically a part or a portion of the object of interest, e.g. the head of a patient.

According to an embodiment of the invention the method further comprises measuring X-ray attenuation data of the region of interest corresponding to the improved spectral X-ray data acquisition. The improved X-ray measurements may by used in any type of dual energy like X-ray data acquisition in order to reduce the effective signal to noise ratio to a minimum.

According to a further embodiment of the invention the step of acquiring attenuation data comprises the step of taking over corresponding data from a standard data set. The standard data set may be e.g. derived from a standard phantom corresponding to the real object of interest. Nowadays, appropriate phantoms are available for all parts of in particular a human body. These phantoms include a composition of different materials, which exhibit at least within the diagnostically relevant energy range a similar X-ray attenuation or X-ray absorption behavior compared to the object of interest. Common materials are for instance water and calcium.

It has to be mentioned that it is not necessary to use a physically existent phantom. For carrying out the described method it is sufficient to use the X-ray attenuation data of such a phantom. These data are publicly available, e.g. on the internet.

According to a further embodiment of the invention the step of acquiring attenuation data comprises the step of accomplishing an initial attenuation measurement of the object. This may provide the advantage that the expected thickness and the material composition of the real object can be evaluated. An approximate knowledge of these X-ray relevant properties of the real object may allow for an even better improvement of the spectral X-ray data acquisition such that the overall signal to noise ratio may be further enhanced.

In case of examining a human patient the initial attenuation measurements may allow for a patient adaptive optimization of the signal-to-noise ratio.

The initial attenuation measurement may be carried out at a plurality of different projection angles of the region of interest such that the measurement corresponds to an initial scanogram or pre-scan of the object under examination. However, typically it is sufficient that the initial attenuation measurement may be accomplished at a comparatively low dose such that the improved quality of a final reconstructed dual-energy three-dimensional image justifies the additional radiation dose even in case the object under examination is a human being.

It has to be pointed out that the initial measurement may be carried out at one or also at two different photon energies. In any case, the thickness and the material composition of the real object should be evaluated with such a precision that the improved quality of the final reconstructed three-dimensional image justifies the additional radiation dose caused by the initial measurement.

According to a further embodiment of the invention the steps of determining the attenuation-base line integrals and calculating the expected signal to noise ratio are carried out for various X-ray beam paths traversing the region of interest. This has the advantage that the SNR maximization procedure is significantly improved because the attenuation data of more than one X-ray beam path traversing the region of interest may be used. This may allow for taking benefit of a detailed and precise knowledge of the expected X-ray attenuation caused by the region of interest. Generally, the following applies: The higher the number of different beam paths is, which are taken into account for the improvement of the first X-ray energy and/or for an improved second X-ray energy, the better the overall SNR optimization process is.

According to a further embodiment of the invention the first spectral X-ray data acquisition and the second spectral X-ray data acquisition are carried out within an energy range between 10 keV and 150 keV. This energy interval represents the diagnostically relevant energy range.

In this respect it has to be noted that all elements, which are typically included in human and/or animal bodies with a significant composition, have a relative low atomic number. Therefore, the characteristic K-edges of the X-ray absorption are well below the lower limit of the given energy range. Therefore, the dependency of the attenuation line integrals from energy is typically a smooth function and can well be represented by two attenuation-base functions, e.g. Photo-effect and Compton-effect.

According to a further embodiment of the invention the first spectral X-ray data acquisition and the second spectral X-ray data acquisition are carried out by means of an X-ray source emitting a polychromatic energy spectrum. Typically, an X-ray tube emits such a polychromatic spectrum, which depends in particular on the acceleration voltage. Also two or more different X-ray sources may be used.

X-ray photons belonging to two distinct energy intervals within a polychromatic energy spectrum may be detected simultaneously. Thereby, appropriate energy resolving detectors have to be employed in order to discriminate the photons belonging to the different X-ray energies from each other.

It has to be mentioned that photons belonging to different X-ray energy intervals may also be detected successively. This may be achieved e.g. by varying the operating conditions of a single X-ray tube, in particular by varying the acceleration voltage, or by using different X-ray filters. In that case, usual X-ray detectors providing no energy resolution may be sufficient.

According to a further embodiment of the invention the first spectral X-ray data acquisition is carried out within a first energy interval. This has the advantage that all photons within this energy interval may be used such that the effective photon count rate and, as a consequence, the corresponding SNR is increased.

According to a further embodiment of the invention the second spectral X-ray data acquisition is carried out within a second energy interval. Thereby, the first energy interval and the second energy interval may be chosen in such a manner that most of the photons, which penetrate the region of interest, contribute to the final image. Therefore, the radiation dose for a patient may be used efficiently for obtaining a high photon count rate within the final dual energy X-ray image.

According to a further embodiment of the invention the first energy interval and the second energy interval are adjacent to each other at an energy value. This energy value represents a threshold energy. This has the advantage that all photons having an energy lying within a wide energy range may be used in order to obtain a dual energy image. The energy separation may be accomplished by an X-ray detector, which comprises an appropriate energy resolution. Thereby, photons having an energy lower than the threshold energy may be counted as a first energy radiation event. Accordingly, photons having an energy higher than the threshold energy may be counted as a second energy radiation event.

According to a further embodiment of the invention the step of selecting an improved spectral X-ray data acquisition comprises varying the threshold energy. This has the advantage that by varying only one parameter both X-ray measurements are varied simultaneously.

According to a further embodiment of the invention the step of determining the attenuation-base line integrals, the step of calculating expected signal to noise ratios and the step of selecting improved spectral X-ray data acquisitions are carried out under the condition of a constant radiation dose. This provides the advantage that the optimization process is carried out under a constant condition, which is highly relevant for patients in order not to increase accidentally and/or unnecessarily the radiation dose.

According to a further embodiment of the invention the method further comprises a step of (a) varying the material and/or the thickness of a filter, which is arranged in each X-ray beam path and/or comprises a step of (b) varying the acceleration voltage of an X-ray tube generating the X-ray beam. Therefore, not only the threshold energy may be optimized but also different parameters of the corresponding X-ray imaging setup may be varied in order to achieve a maximum SNR of the resultant dual energy image.

It has to be mentioned that the described method is not limited to a dual-energy X-ray imaging. Since both modern detectors provide a high-energy resolution and further modern data processing devices provide a high computing power, the described method can also be accomplished with three or even more spectral different X-ray data acquisitions respective X-ray measurements. Therefore, even more informative X-ray images may be generated.

The above-mentioned need may further be met by a data processing device for reducing statistical noise of X-ray attenuation data related to two spectral different X-ray data acquisitions, a first spectral X-ray data acquisition and a second spectral X-ray data acquisition, in particular for enhancing the overall signal to noise ratio for dual energy X-ray imaging.

According to this aspect of the invention the data processing device comprises a memory for storing given X-ray attenuation data representing the X-ray attenuation behavior of a region of interest within an object of interest.

The data processing device further comprises a data processor, which is adapted for performing the following operation:
(a) Determining a first attenuation-base line integral for the first spectral X-ray data acquisition and a second attenuation-base line integral for the second spectral X-ray data acquisition, respectively, for a predetermined X-ray beam path traversing the region of interest, (b) calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively, (c) repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition, and (d) selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral.

According to a further embodiment of the invention the data processor is further adapted to carry out the step of processing measured X-ray attenuation data of the region of interest corresponding to the improved spectral X-ray data acquisitions. This means, that apart from optimizing the spectrally-sensitive X-ray measurements, in particular the threshold energy, the data processor can also be used to carry out a digital image processing which is necessary in order to generate a viewable image based on a plurality of acquired X-ray attenuation data.

The above-mentioned need may further be met by a radiography system for generating X-ray images of a region of interest based on X-ray attenuation data related to two spectral different X-ray data acquisitions, a first spectral X-ray data acquisition and a second spectral X-ray data acquisition.

The radiography system comprises a radiation source adapted for emitting a radiation beam, a radiation detector adapted for detecting the radiation beam after the beam has passed the region of interest, a memory for storing given X-ray attenuation data representing the X-ray attenuation behavior of the region of interest within an object of interest, and a data processor. The data processor is adapted for performing the following operation:
(a) Determining a first attenuation-base line integral for the first spectral X-ray data acquisition and a second attenuation-base line integral for the second spectral X-ray data acquisition, respectively, for a predetermined X-ray beam path traversing the region of interest, (b) calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively, (c) repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition, and (d) selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral.

The radiation source may be a conventional X-ray source. Preferably, the radiation source is adapted to emit a polychromatic X-ray radiation beam. The radiation detector can be formed of a single radiation detector, a plurality of radiation detectors or a detector array. Preferably, the radiation detector comprises an energy resolution such that photons within either the first X-ray energy interval or the second X-ray energy interval may be detected without changing the setting or the operation mode of the detector.

The radiographic system may be e.g. a dual energy computed tomography (CT) system generating 3D images. However, the described noise reduction is also applicable for dual energy computed radiography imaging systems, which typically produce 2D images like e.g. angiographic X-ray imaging systems. In any case, the dual energy X-ray imaging may be carried out with or without contrast agents.

According to an embodiment of the invention the radiation detector comprises an energy resolution. This means, that the radiation detector and, if necessary, electronic equipment arranged downstream with respect to the detector is capable of discriminating a photon detection into one of two different events. Preferably, photons having an energy lower than the threshold energy may be counted as a first energy radiation event. Accordingly, photons having an energy higher than the threshold energy may be counted as a second energy radiation event.

The radiation detector may be a detector comprising an energy integration e.g. a scintillation detector. This causes the detector output to be proportional to the energy of the detected photon. The radiation detector may alternatively be an energy discriminating detector, wherein two types of signals are outputted depending on whether the energy of a detected photon is within a first energy interval or the energy of the detected photon is within a second energy interval.

The above-mentioned need may further be met by a computer-readable medium on which there is stored a computer program for reducing statistical noise of X-ray attenuation data related to two spectral different X-ray data acquisitions, a first spectral X-ray data acquisition and a second spectral X-ray data acquisition. The computer program, when being executed by a processor, is adapted for performing an operation comprising steps of exemplary embodiments of the above-described method.

The above-mentioned need may further be met by a program element for reducing statistical noise of X-ray attenuation data related to two spectral different X-ray data acquisitions, a first spectral X-ray data acquisition and a second spectral X-ray data acquisition. The program element, when being executed by a processor, is adapted for performing an operation comprising steps of exemplary embodiments of the above-described method.

The program element may be written in any suitable programming language, such as, for example, C++ and may be stored on a computer-readable medium, such as a CD-ROM. Also, the computer program may be available from a network, such as the World Wide Web, from which it may be downloaded into image processing units or processors, or any suitable computer.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one subject matter also any combination between features relating to different subject matters, in particular between features of the apparatus type claims and features of the method type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

The illustration in the drawing is schematically. It is noted that in different drawings, similar or identical elements are provided with the same reference signs or with reference signs, which are different from the corresponding reference signs only within the first digit.

In the following there will be first given some theoretical background information related to the influence of photon statistics on the SNR in dual-energy imaging.

Dual energy X-ray imaging introduces an additional processing step into the image processing steps of conventional X-ray or computed tomography (CT) systems. This processing step is based on the important insight, that the energy dependence of the mass attenuation coefficient μ(E) of matter in the energy range of diagnostic interest (i.e. the energy range between approximately 10 keV and 150 keV) can be well approximated by a linear combination of only two attenuation base functions $\mu_1(E)$ and $\mu_2(E)$. This can be understood from a physical point of view as the sum of the total cross-sections for the photo effect and for Compton scattering.

However, this behavior can also be described by the combination of the mass attenuation of water and calcium. These base materials are often more convenient for physicians in order to understand the X-ray attenuation behavior of a live human and/or animal tissue since theses materials are important constituents of human tissue.

The above-mentioned processing step involves the solution of the following set of non-linear equations:

$$M_1 = C_1 \int_0^{E_T} \Phi_1(E) e^{-A_1 \mu_1(E) - A_2 \mu_2(E)} D_1(E) dE = f_1(A_1, A_2) \quad (1a)$$

$$M_2 = C_2 \int_{E_T}^{\infty} \Phi_2(E) e^{-A_1 \mu_1(E) - A_2 \mu_2(E)} D_2(E) dE = f_2(A_1, A_2) \quad (1b)$$

Here, $M_1$ and $M_2$ are the number of photons, which are detected in the energy interval ranging from 0 to $E_T$ and from $E_T$ to ∞, respectively. $C_1$ and $C_2$ are coefficients obtained through a calibration procedure, respectively. $E_T$ is a threshold energy separating each photon detection event into either an event contributing to $M_1$ or an event contributing to $M_2$. In order to avoid excessive detector noise, a low-energy noise threshold must be set in addition to $E_T$.

In the above given formulae $\Phi_1(E)$ and $\Phi_2(E)$ represent the filtered photon number spectra within the two above-mentioned energy intervals, respectively, which photons impinge on the object of interest. $D_1(E)$ and $D_2(E)$ denote the efficiency of the corresponding detector for the two energy intervals, respectively. $A_1$ and $A_2$ are the mass attenuation line integrals representing the object path under consideration.

Both formula (1a) and (1b) can be written as functions which only depend on $A_1$ and on $A_2$.

It can be shown that the variances $\sigma_{Ai}^2$ of the derived quantities $A_i$ are related to the signal to noise ratios $SNR_1$ and $SNR_2$ of the original measurements $M_i$ through:

$$\sigma_{A_1}^2 = \frac{\mu_{22}^2/SNR_1^2 + \mu_{12}^2/SNR_2^2}{(\mu_{11}\mu_{22} - \mu_{12}\mu_{21})^2} \quad (2a)$$

$$\sigma_{A_2}^2 = \frac{\mu_{21}^2/SNR_1^2 + \mu_{11}^2/SNR_2^2}{(\mu_{11}\mu_{22} - \mu_{12}\mu_{21})^2} \quad (2b)$$

Thereby, $\mu_{ij} \equiv -\frac{\partial \ln(M_i)}{\partial A_j}, (i, j = 1, 2)$.

Here, $\mu_{ij}$ represent effective attenuation coefficients over the spectra transmitted through the object. The formulae (2a) and (2b) may be derived from the above-given formulae (1a) and (1b) by applying the so-called Gauss error propagation rule. $\sigma_{Ai}$ is directly proportional to the width of a Gauss distribution depicting the distribution of the mass attenuation line integrals $A_i$ as a function of the statistical distribution of the photon counts.

As one can easily see from the above given formulas, the maximal SNR for each of the two images strongly depends on the threshold energy $E_T$. This means that the optimal $E_T$ is different for the reconstructed photo or Compton or for the water or calcium images. However, the spectra and base materials often affect the noise mainly through the denominators in the above formulae which are equal to the so-called "spectral quality factor" given by $SQF=(\mu_{11}\mu_{22}-\mu_{12}\mu_{21})^2$. Therefore, the optimal thresholds for photo and Compton images (or water and calcium images) will be similar.

According to an embodiment of the invention described hereinafter a minimization of the above-given variances and a maximization of the corresponding SNR is achieved by optimizing the threshold energy $E_T$ under the condition of constant patient dose.

In has to be pointed out that such an optimization procedure could partially be combined with simulated variations of a material typically used for X-ray filters materials and/or with simulated variations of the thicknesses of such materials. Furthermore, an optimization procedure could also be combined with simulations of variations in the tube voltage.

Figure 1:
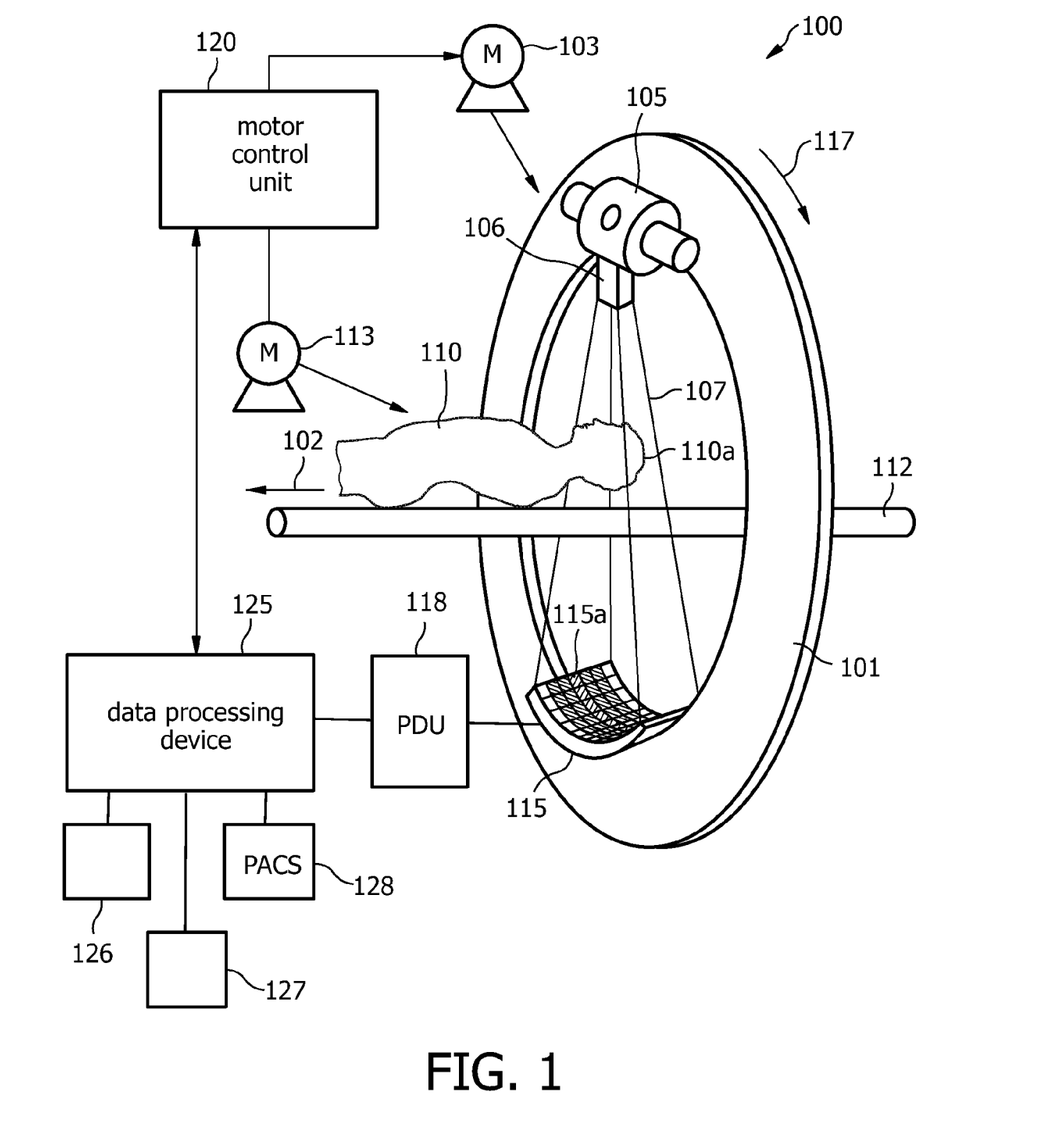
FIG. 1 shows a simplified schematic representation of a dual energy computer tomography (CT) system.

FIG. 1 shows a computer tomography apparatus 100, which is also called a CT scanner. The CT scanner 100 comprises a gantry 101, which is rotatable around a rotational axis 102. The gantry 101 is driven by means of a motor 103.

Reference numeral 105 designates a source of radiation such as an X-ray source, which emits polychromatic radiation. The CT scanner 100 further comprises an aperture system 106, which forms the radiation beam emitted from the radiation source 105 into a polychromatic radiation beam 107. The spectral distribution of the radiation beam emitted from the radiation source 105 may further be changed by a filter element (not shown), which is arranged close to the aperture system 106.

The radiation beam 107, which may by a cone-shaped or a fan-shaped beam 107, is directed such that it penetrates a region of interest 110a. According to the embodiment described herewith, the region of interest is a head 110a of a patient 110.

The patient 110 is positioned on a table 112. The patient's head 110a is arranged in the center of the gantry 101, which represents the examination region of the CT scanner 100. After penetrating the region of interest 110a the polychromatic radiation beam 107 impinges onto a radiation detector 115. In order to be able to separate each photon detection event into a low-energy photon event or into a high-energy photon event, the radiation detector 115 comprises an energy resolution.

As may be taken from FIG. 1, the energy-resolving detector 115 is arranged on the gantry 101 opposite to the source of radiation 105. The detector 115 comprises a plurality of detector elements 115a wherein each is capable of detecting X-ray photons, which have been scattered by or passed through the head 110a of the patient 110.

During scanning the region of interest 110a, the X-ray source 105, the aperture system 106 and the detector 115 are rotated together with the gantry 101 in a rotation direction indicated by an arrow 117. For rotation of the gantry 101, the motor 103 is connected to a motor control unit 120 which itself is connected to a data processing device 125. The data processing device 125 includes a reconstruction unit, which may be realized by means of hardware and/or by means of software. The reconstruction unit is adapted to reconstruct a 3D image based on a plurality of 2D images obtained under various observation angles.

Furthermore, the data processing device 125 serves also as a control unit, which communicates with the motor control unit 120 in order to coordinate the movement of the gantry 101 with the movement of the table 112. A linear displacement of the table 112 is carried out by a motor 113, which is also connected to the motor control unit 120.

The CT scanner 100 captures computer tomography data of the head 110a. Thereby, the gantry 101 rotates and in the same time the table 112 is shifted linearly parallel to the rotational axis 102 such that a helical scan of the region of interest 110a is performed.

It should be noted that it is also possible to perform a circular scan, where there is no displacement in a direction parallel to the rotational axis 102, but only the rotation of the gantry 101 around the rotational axis 102. Thereby, slices of the head 110a may be measured with high accuracy.

The detector 115 is coupled to a pulse discriminator unit 118 allowing for a separation of each photon-detection event into a low-energy event or alternatively into a high-energy event. The pulse discriminator unit 118 is coupled to the data processing device 125, which is capable, based on the corresponding low-energy photon counts and on the corresponding high-energy photon counts, to reconstruct two different 3D images. These images may be combined by means of the data processing device 125 in order to generate a final 3D image. Alternatively, the two images may be outputted separately such that a physician is able to interpret the two images.

It has to be mentioned that in between the detector 115 and the data processing device 125 there may be connected further electronic devices, which allow for a real time data handling of the acquired projection data.

In order to observe the reconstructed images a display 126 is provided, which is coupled to the data processing device 125. Additionally, the two images may also be printed out by a printer 127, which is also coupled to the data processing device 125. Further, the data processing device 125 may also be coupled to a picture archiving and communications system 128 (PACS).

It should be noted that monitor 126, the printer 127 and/or other devices supplied within the CT scanner 100 might be arranged local to the computer tomography apparatus 100. Alternatively, these components may be remote from the CT scanner 100, such as elsewhere within an institution or hospital, or in an entirely different location linked to the CT scanner 100 via one or more configurable networks, such as the Internet, virtual private networks and so forth.

Figure 2:
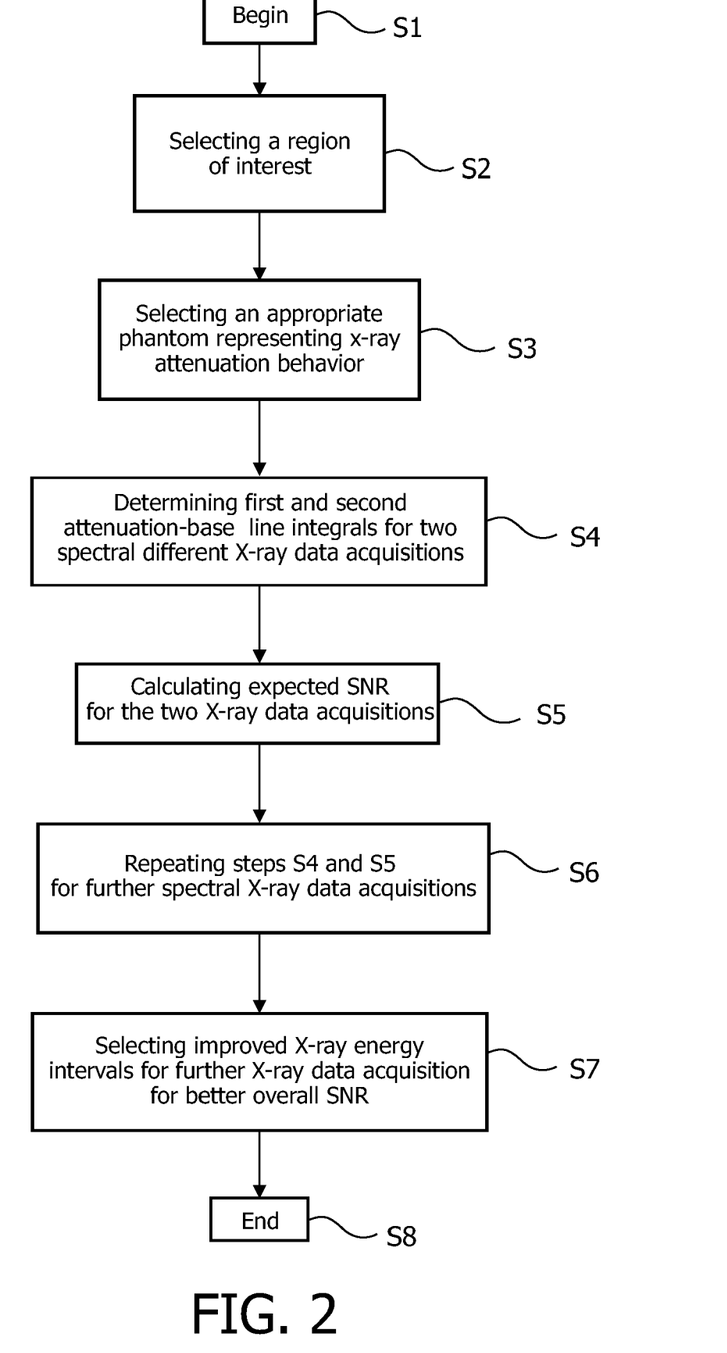
FIG. 2 shows a flow chart on a method for reducing the statistical noise of x-ray attenuation data related to two spectral different X-ray data acquisitions.

FIG. 2 shows a flow chart on an exemplary method for reducing statistical noise of X-ray attenuation data related to two different X-ray energy intervals, a first X-ray energy intervals and a second X-ray energy intervals, in particular for enhancing the overall signal to noise ratio for dual energy X-ray imaging. The method starts with a step S1.

In step S2 there is selected a region of interest within an object of interest. The region of interest may either be a part of the object of interest, e.g. a human body, or the entire object.

In step S3 there is selected an appropriate phantom. The phantom represents the X-ray attenuation behavior of the region of interest. Appropriate phantoms are available for all parts of in particular a human body. These phantoms include a composition of different materials, which exhibit at least within the diagnostically relevant energy interval a similar X-ray attenuation or X-ray absorption behavior.

It has to be pointed out that instead of or in addition to using a phantom in order to extract information on the expected X-ray attenuation of the region of interest it is also possible to accomplish an initial attenuation measurement of the real object. This may provide the advantage that the expected thickness and the material composition of the real object can be evaluated. In case of examining a human patient the initial attenuation measurements may allow for a patient adaptive optimization of the signal-to-noise ratio.

In step S4 there are determined a first attenuation-base line integral for the first spectral X-ray data acquisition and a second attenuation-base line integral for the second spectral X-ray data acquisition, respectively. Both attenuation-base line integrals are determined for a predetermined X-ray beam path traversing the phantom.

In step S5 there is calculated an expected first signal to noise ratio for the first attenuation-base line integral and an expected second signal to noise ratio for the second attenuation-base line integral based on given signal to noise ratios for the first and the second spectral X-ray data acquisition, respectively.

In step S6 there are repeated the above-mentioned steps of determining the attenuation-base line integrals and calculating the expected signal to noise ratio for at least a further first spectral X-ray data acquisition being different from the first spectral X-ray data acquisition and/or for at least a further second spectral X-ray data acquisition being different from the second spectral X-ray data acquisition. Thereby, the dependency of the two signal to noise ratios is determined for each spectral X-ray data acquisition.

The energy dependence of the SNR can be illustrated very easily as a function of one parameter only. This is the case if the two spectral different X-ray data acquisitions are carried out within two adjacent X-ray energy intervals, which are separated from each other by a so-called threshold energy $E_T$. The assignment of two neighboring energy intervals to then two spectral data acquisitions, respectively, has the further advantage that all photons, which penetrate the region of interest, may be used for the dual-energy imaging.

In step S7 there is selected an improved first spectral X-ray data acquisition and/or an improved second spectral X-ray data acquisition in order to enhance the overall signal to noise ratio of an X-ray image, which is based on the first attenuation-base line integral and on the second attenuation-base line integral.

Finally, the method ends with a step S8.

The improved first spectral X-ray data acquisition and/or the improved second spectral X-ray data acquisition may be used for dual-energy imaging of the region of interest 110a. Since the above-described method can be accomplished well before a physically X-ray imaging, the actual dual-energy X-ray imaging can be carried out without deferment. Therefore, the realization of the invention is based on a maximization process of the SNR of simulated data with respect to the variable energy threshold $E_T$.

Figure 3:
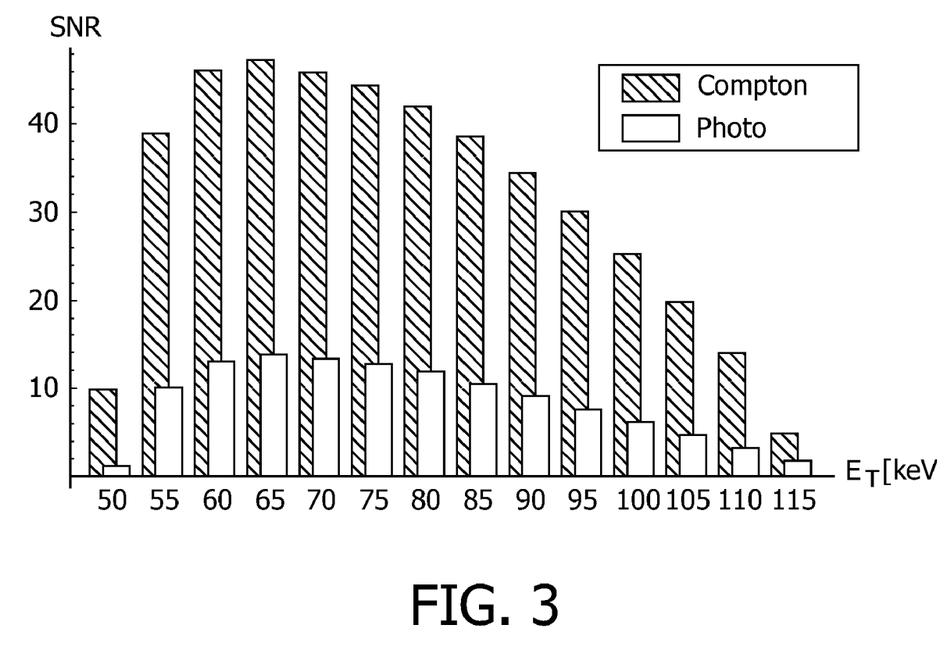
FIG. 3 shows a diagram depicting an exemplary behavior of the SNR of two different images obtained when a threshold energy $E_T$ separating two energy windows is varied.

FIG. 3 shows an exemplary diagram depicting an exemplary behavior of the SNR of two different images obtained with different X-ray energy intervals when a threshold Energy $E_T$ separating the two energy intervals is varied. The graph shows the SNR of the photo/Compton signals as a function of the energy threshold $E_T$. The exemplary diagram shows the results of an optimization based on the above-given formulae in the case of a phantom composed of 20 cm of water and 2 cm of calcium. The anode current was set to 100 mA and the X-ray tube voltage was considered to be 120 kV. As one can see from the depicted behavior of the SNR the optimal thresholds for both components are about 65 keV.

It has to be pointed out that the inventors also give a reason why the maxima for the two SNR in diagram 3 are located approximately at the same value for the threshold energy. As can be seen from formulae (2a) and (2b), the values of the variances $\sigma_{Ai}^2$ depend predominately on the above-given SQF, which is the same for $\sigma_{A1}^2$ and for $\sigma_{A2}^2$. The enumerator respective the numerator of the variances $\sigma_{A1}^2$ and for $\sigma_{A2}^2$ exhibits a weak dependence on the threshold energy, respectively. This can be seen from the fact that each photon from a total number of photons has to be counted either as a low-energy event or as a high-energy event. This means that each photon increases either $SNR_1$ or $SNR_2$. Since the inverted $SNR_i$ values are summed up for $\sigma_{A1}^2$ as well as for $\sigma_{A2}^2$, a variation of $E_T$ affects the variances $\sigma_{A1}^2$ as well as $\sigma_{A2}^2$ only weakly.

Figure 4:
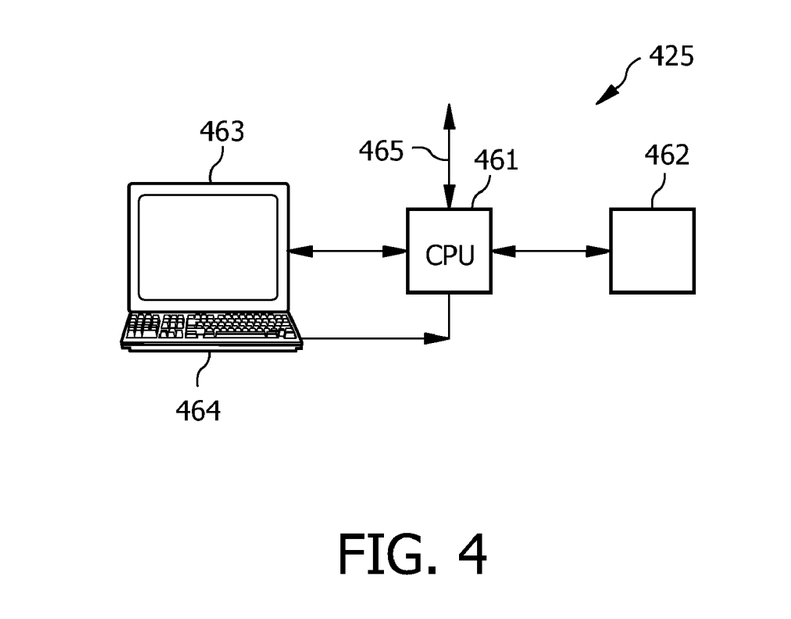
FIG. 4 shows an image processing device for executing an exemplary embodiment of a method in accordance with the present invention.

FIG. 4 depicts an exemplary embodiment of a data processing device 425 according to the present invention for executing an exemplary embodiment of a method in accordance with the present invention. The data processing device 425 comprises a central processing unit (CPU) or image processor 461. The image processor 461 is connected to a memory 462 for temporally storing acquired projection data. Via a bus system 465 the image processor 461 is connected to a plurality of input/output network or diagnosis devices, such as a CT scanner. Furthermore, the image processor 461 is connected to a display device 463, for example a computer monitor, for displaying information or one or more images reconstructed by the image processor 461. An operator or user may interact with the image processor 461 via a keyboard 564 and/or any other output devices, which are not depicted in FIG. 4.

It has to be pointed out the invention is not limited to dual energy computed tomography system generating 3D images. The described noise reduction is also applicable for dual energy computed radiography imaging systems, which typically produce 2D images like e.g. angiographic X-ray imaging systems. In any case, the dual energy X-ray imaging may be carried out with or without contrast agents.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

LIST OF REFERENCE SIGNS 100 computer tomography apparatus/CT scanner
101 gantry
102 rotational axis
103 motor
105 polychromatic X-ray source
106 aperture system
107 polychromatic radiation beam
110 object of interest/patient
110a region of interest/head of patient
112 table
113 motor
115 energy resolving radiation detector
115a detector elements
117 rotation direction
118 Pulse discriminator unit
120 motor control unit
125 data processing device (incl. reconstruction unit)
126 monitor
127 printer
128 Picture archiving and communication system (PACS)
S1 step 1
S2 step 2
S3 step 3
S4 step 4
S5 step 5
S6 step 6
S7 step 7
S8 step 8
425 data processing device
461 central processing unit/image processor
462 memory
463 display device
464 keyboard
465 bus system The invention claim is:

1. A method for reducing statistical noise of X-ray attenuation data related to two spectral different X-ray data acquisition, a first spectral X-ray data acquisition and a second spectral X-ray data acquisition, in particular for enhancing the overall signal to noise ratio for dual energy X-ray imaging, the method comprising the steps of
acquiring attenuation data representing the X-ray attenuation behavior of a region of interest within an object of interest,
determining a first attenuation-base line integral for the first spectral X-ray data acquisition and a second attenuation-base line integral for the second spectral X-ray data acquisition, respectively, for a predetermined X-ray beam path traversing the region of interest using a data processing device,
calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively, using the data processing device,
repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition,
selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral using a data processing device.

2. The method according to claim 1, further comprising measuring X-ray attenuation data of the region of interest corresponding to the improved spectral X-ray data acquisition.

3. The method according to claim 1, wherein
the step of acquiring attenuation data comprises the step of taking over corresponding data from a standard data set.

4. The method according to claim 1, wherein
the step of acquiring attenuation data comprises
accomplishing an initial attenuation measurement of the object.

5. The method according to claim 1, wherein
the steps of determining the attenuation-base line integrals and calculating the expected signal to noise ratios are carried out for various X-ray beam paths traversing the region of interest.

6. The method according to claim 1, wherein
the first spectral X-ray data acquisition and the second spectral X-ray data acquisition are carried out within an energy range between 10 keV and 150 keV.

7. The method according to claim 1, wherein
the first spectral X-ray data acquisition and the second spectral X-ray data acquisition are carried out by means of an X-ray source emitting a polychromatic energy spectrum.

8. The method according to claim 1, wherein
the first spectral X-ray data acquisition is carried out within a first energy interval.

9. The method according to claim 8, wherein
the second spectral X-ray data acquisition is carried out within a second energy interval.

10. The method according to claim 9, wherein on the energy scale
the first energy interval and the second energy interval are adjacent to each other at an energy value representing a threshold energy ($E_T$).

11. The method according to claim 10, wherein
the step of selecting an improved spectral X-ray data acquisition comprises varying the threshold energy ($E_T$).

12. The method according to claim 1, wherein at least the step of determining the attenuation-base line integrals, the step of calculating expected signal to noise ratios and the step of selecting improved spectral X-ray data acquisitions are carried out under the condition of a constant radiation dose.

13. The method according to claim 12, further comprising a step of
varying the material and/or the thickness of a filter which is arranged in each X-ray beam path and/or
varying the acceleration voltage of an X-ray tube generating the X-ray beam.

14. A data processing device for reducing statistical noise of X-ray attenuation data related to two spectral different X-ray data acquisitions, a first spectral X-ray data acquisition and a second spectral X-ray data acquisition, in particular for enhancing the overall signal to noise ratio for dual energy X-ray imaging, the data processing device comprising
- a memory for storing given X-ray attenuation data representing the X-ray attenuation behavior of a region of interest within an object of interest, and
- a data processor, which is adapted for performing the following operation:
- determining a first attenuation-base line integral for the first spectral X-ray data acquisition and a second attenuation-base line integral for the second spectral X-ray data acquisition, respectively, for a predetermined X-ray beam path traversing the region of interest,
- calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively,
- repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition, and
- selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral.

15. The data processor device according to claim 14, wherein the data processor is further adapted to carry out the step of
- processing measured X-ray attenuation data of the region of interest corresponding to the improved spectral X-ray data acquisitions.

16. A radiography system for generating X-ray images of a region of interest based on X-ray attenuation data related to two spectral different X-ray data acquisitions, a first spectral X-ray data acquisition and a second spectral X-ray data acquisition, the radiography system comprising
- a radiation source adapted for emitting a radiation beam,
- a radiation detector adapted for detecting the radiation beam after the beam has passed the region of interest,
- a memory for storing given X-ray attenuation data representing the X-ray attenuation behavior of the region of interest within an object of interest, and
- a data processor, which is adapted for performing the following operation:
- determining a first attenuation-base line integral for the first spectral X-ray data acquisition and a second attenuation-base line integral for the second spectral X-ray data acquisition, respectively, for a predetermined X-ray beam path traversing the region of interest,
- calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively,
- repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition, and
- selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral.

17. The radiography system according to claim 16, wherein the radiation detector comprises an energy resolution.

18. A non-transitory computer-readable medium on which there is stored a computer program for reducing statistical noise of X-ray attenuation data related to two spectral different X-ray data acquisitions, a first spectral X-ray data acquisition and a second spectral X-ray data acquisition, which computer program, when being executed by a processor, is adapted for performing the following operation:
- determining a first attenuation-base line integral for the first spectral X-ray data acquisition and a second attenuation-base line integral for the second spectral X-ray data acquisition, respectively, for a predetermined X-ray beam path traversing a region of interest using a data processing device,
- calculating an expected first signal to noise ratio for the first attenuation-base line integral and an expected second signal to noise ratio for the second attenuation-base line integral based on given signal to noise ratios for the first spectral X-ray data acquisition and for the second spectral X-ray data acquisition, respectively using a data processing device,
- repeating the above mentioned steps of determining the attenuation-base line integrals and calculating the expected signal to noise ratio for a further first spectral X-ray data acquisition being different from the first spectral X-ray data acquisition and/or for a further second spectral X-ray data acquisition being different from the second spectral X-ray data acquisition, and
- selecting an improved first spectral X-ray data acquisition and/or an improved second spectral X-ray data acquisition in order to enhance the overall signal to noise ratio of an X-ray image which is based on the first attenuation-base line integral and on the second attenuation-base line integral using a data processing device.

* * * * *